United States Patent
Schröder et al.

(10) Patent No.: US 7,311,759 B2
(45) Date of Patent: Dec. 25, 2007

(54) PROCESS FOR PURIFYING OFF-GASES OF A MELAMINE PLANT

(75) Inventors: Frank Schröder, Albrechtshain (DE); Hartmut Bucka, Eggendorf (AT); Christoph Neumüller, Linz (AT); Gerhard Coufal, Leonding (AT)

(73) Assignee: Ami - Agrolinz Melamine International GmbH, Linz (AT)

( * ) Notice: Subject to any disclaimer, the term of this patent is extended or adjusted under 35 U.S.C. 154(b) by 505 days.

(21) Appl. No.: 10/495,310

(22) PCT Filed: Nov. 14, 2002

(86) PCT No.: PCT/DE02/04250

§ 371 (c)(1),
(2), (4) Date: Sep. 30, 2004

(87) PCT Pub. No.: WO03/045538

PCT Pub. Date: Jun. 5, 2003

(65) Prior Publication Data

US 2005/0056147 A1    Mar. 17, 2005

(30) Foreign Application Priority Data

Nov. 16, 2001 (AT) .............................. A 1806/2001
Jun. 25, 2002 (DE) .............................. 102 29 101

(51) Int. Cl.
C07D 251/60 (2006.01)
C07D 251/62 (2006.01)
C07D 55/24 (2006.01)
B01D 47/00 (2006.01)
B01D 53/14 (2006.01)
C07F 3/00 (2006.01)
C08G 79/00 (2006.01)

(52) U.S. Cl. .................. 95/187; 544/200; 544/201; 544/203; 55/84; 260/1; 260/665 B; 260/665 G; 260/665 R

(58) Field of Classification Search ................ 95/187; 544/200–201; 260/249.7
See application file for complete search history.

(56) References Cited

U.S. PATENT DOCUMENTS

| | | | | | |
|---|---|---|---|---|---|
| 3,155,723 | A | * | 11/1964 | Saffian et al. ............... | 564/71 |
| 3,386,999 | A | * | 6/1968 | Manes ....................... | 544/201 |
| 3,700,672 | A | * | 10/1972 | Kokubo et al. ............. | 544/201 |
| 4,138,560 | A | * | 2/1979 | Hillenbrand et al. ........ | 544/203 |
| 4,565,867 | A | * | 1/1986 | Thomas et al. .............. | 544/201 |
| 5,514,796 | A | * | 5/1996 | Best et al. .................. | 544/201 |
| 6,245,909 | B1 | | 6/2001 | Van Wijck | |

FOREIGN PATENT DOCUMENTS

| | | |
|---|---|---|
| EP | 0 459 962 A1 | 12/1991 |
| EP | 0 711 729 A1 | 5/1996 |
| JP | 53-81898 | 7/1978 |
| RU | 2 161 608 C2 | 1/2001 |
| SU | 863 746 A1 | 9/1981 |
| SU | 863746 | 9/1981 |
| SU | 1 074 161 A1 | 1/1992 |
| SU | 1074161 A1 | 1/1992 |

OTHER PUBLICATIONS

English translation of International Preliminary Examination Report for International Application No. PCT/DE2002/004250; International Filing Date of Nov. 14, 2002; dated Jul. 11, 2003.
International Search Report of PCT/DE02/04250, dated Mar. 28, 2003.
International Preliminary Examination Report of PCT/DE02/04250, dated Jul. 11, 2003.
Russian Decision to grant dated Dec. 18, 2006, for corresponding application.

* cited by examiner

*Primary Examiner*—Jason Greene
*Assistant Examiner*—Ives Wu
(74) *Attorney, Agent, or Firm*—Christie, Parker & Hale, LLP

(57) ABSTRACT

A two-stage process is provided for purifying off-gases from a high-pressure melamine plant. In the first stage, the off-gases are contacted with a recirculated urea melt containing melamine precursors and $NH_3$. In the second stage, the off-gases are contacted with a fresh urea melt.

15 Claims, 2 Drawing Sheets

PROCESS FOR PURIFYING OFF-GASES OF A MELAMINE PLANT

CROSS-REFERENCE TO RELATED APPLICATION

This application is a National Phase Patent Application of International Application Number PCT/DE02/04250, filed on Nov. 14, 2002, which claims priority of Austrian Patent Application Number A 1806/2001, filed on Nov. 16, 2001, and German Patent Application Number 102 29 101.2, filed on Jun. 25, 2002.

FIELD OF THE INVENTION

The invention relates to a two-stage process for purifying off-gases from a high-pressure melamine plant having a melamine precursor-containing and $NH_3$-containing circulated urea melt in a first stage and fresh urea melt in a second stage.

BACKGROUND

In the high-pressure process for preparing melamine, generally urea and ammonia are reacted at temperatures between about 320 and 450° C. and pressures between about 50 and 600 bar to form liquid melamine and off-gas principally consisting of ammonia, carbon dioxide and small amounts of gaseous melamine and other minor components. After the melamine melt has been separated off from the off-gas, this melamine melt is worked up by various processes for preparing pure melamine, while the off-gas is preferably recirculated to a urea plant.

Before recirculating the off-gas to the urea plant, however, this off-gas must be freed from the melamine content and the other minor components, since these are unwanted in the urea plant.

According to U.S. Pat. No. 3,700,672, the off-gas is brought into contact with fresh urea in countercurrent in a single stage at temperatures between 135 and 250° C. and approximately at the synthesis pressure of the melamine reactor, that is to say at 50 to 200 bar, and in this process is freed from the melamine present and the other minor components. The melamine and the minor components in the off-gas are absorbed in the fresh urea melt, thus recovered from the off-gas and then recirculated back to the melamine reactor. As a result the melamine yield in the melamine synthesis reactor can be increased. In the process employed according to U.S. Pat. No. 3,700,672, the maximum operating temperature for the off-gas scrubbing is 250° C. This upper temperature limit is required according to U.S. Pat. No. 3,700,672, since above 250° C., solid by-products are formed which interfere in the recycling of the urea into the melamine synthesis reactor, and gaseous by-products are formed which are unwanted in the off-gas.

The disadvantage of said process is that as a result of the single-stage contacting of off-gas and urea melt, the exit temperatures both of the purified off-gas at the scrubber head, and of the urea melt enriched with melamine and other off-gas minor components in the scrubber bottom phase must be approximately the same. To maintain the required low operating temperatures in the off-gas scrubber, it is necessary, therefore, to remove a large amount of the heat introduced into the scrubber with the hot off-gas as waste heat via a cooler. Although this waste heat can be used to form steam, in the energy balance of the melamine synthesis process, it denotes an energy loss, since the urea melt exiting from the scrubber at a maximum 250° C. must be reheated in the melamine reactor to the synthesis temperature of about 380° C. This means that the loss of energy in the scrubber must be compensated for by feeding heating energy to the synthesis reactor.

A further disadvantage of low operating temperatures in the scrubber bottom phase is the formation of by-products. These are those substances which form exothermically in the scrubber, that is to say with release of heat, from the ammonia and the carbon dioxide of the off-gas, for example carbamate and water. As a result of formation of these substances, heat is produced in the scrubber at a low temperature level, which must be removed as waste heat. These by-products must later be decomposed in the melamine reactor into the starting materials ammonia and carbon dioxide at a high temperature level by supplying heating energy. This energy transport in the form of chemical energy from the synthesis reactor to the scrubber is a great loss.

The requirements of an optimum off-gas scrubber are therefore many: firstly, the off-gases coming from the melamine reactor are to be freed as completely as possible from the melamine and the other minor substances, secondly, the energy efficiency of the melamine synthesis process is to be improved by better utilization of the off-gas heat. The object thus posed is to find a process which takes these requirements into account.

SUMMARY OF THE INVENTION

Unexpectedly, it was possible to develop a process, using which not only the off-gases can be efficiently purified before their recirculation to the urea plant, but also, by converting heat energy of the off-gases into chemical energy of melamine precursors in the scrubber, the energy efficiency of the melamine process can be increased.

The present invention therefore relates to a process for purifying off-gases from a high-pressure melamine plant with formation of melamine precursors which is characterized in that the off-gases are brought into contact in a first stage with a melamine-precursor-containing and $NH_3$-containing recirculated urea melt and in a second stage with fresh urea melt.

The inventive off-gas purification offers numerous advantages which will be explained below:

The off-gas purification in a first relatively hot stage with melamine-precursor-containing and $NH_3$-containing recirculated urea melt and in a second relatively cold stage with fresh urea melt improves, compared with single-stage contacting at constant temperature, the degree of separation of the minor components present in the off-gases so that under otherwise identical operating conditions purer off-gases can be taken off at the top of the two-stage off-gas scrubber compared with a single-stage scrubber. In addition, by means of the prescrubbing achieved in the first stage with melamine-precursor-containing and $NH_3$-containing recirculated urea melt as early as at the transition of the off-gases from the first to the second stage, the solids content in the off-gases is decreased to the point that the use of highly efficient scrubbing elements, for example sieve trays or valve trays, for fine separation at the scrubber top is possible without plugging or blockage of these elements occurring, as a result of which, in turn, the efficiency of the off-gas purification improves.

By means of the inventive off-gas purification it is in addition possible to operate the scrubber bottom at a different, that is to say higher, temperature than the scrubber top.

As a result the urea in the scrubber bottom can be more intensively preheated compared with a single-stage process in which off-gas exit temperature and urea exit temperature are necessarily approximately equal, which means an improvement in the energy balance of the melamine synthesis reactor/off-gas scrubber system.

Furthermore, it is possible in this manner to convert some of the heat introduced with the off-gases into chemical energy of melamine precursors instead of removing it as useless waste heat via a cooler. Melamine precursors are taken to mean those substances which form endothermically, that is to say with heat consumption from the starting material urea, in the off-gas scrubber under certain circumstances, for example ammeline, ammelide or cyanuric acid. These substances are then, together with the urea melt preheated in the scrubber, fed to the melamine synthesis reactor and are there reacted to form melamine in an endothermic reaction. However, since less energy is required for melamine formation starting from the melamine precursors than for melamine formation starting from urea, in this manner the heating energy required in the melamine synthesis reactor can be reduced. By supplying carbon dioxide at the transition of the off-gases into the melamine-precursor-containing and $NH_3$-containing recirculated urea melt of the first stage, the melamine precursor formation can be further increased.

An additional advantage of the higher operating temperature in the first stage is that less carbamate and water are formed from the ammonia and carbon dioxide of the off-gases.

DETAILED DESCRIPTION

Figure 2:
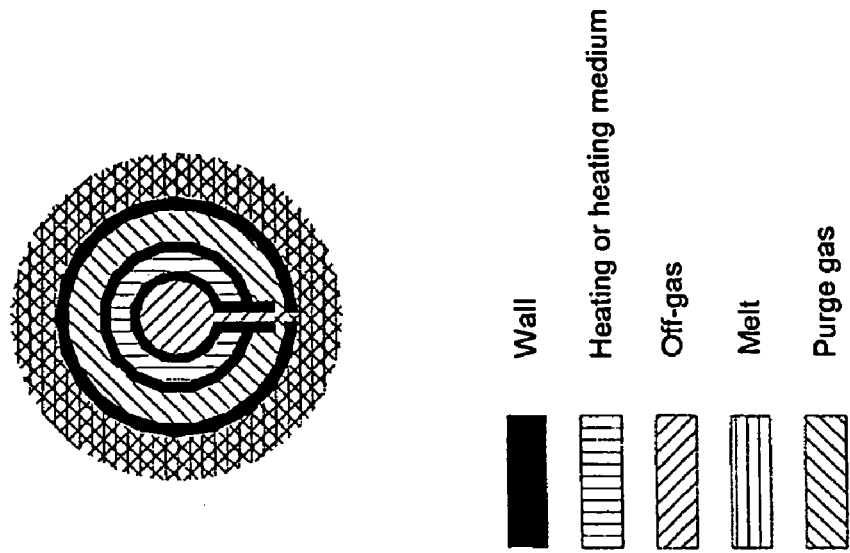
FIG. 2 is a schematic diagram of the off-gas distributor Ae shown in section.

The off-gases to be purified originate from any type of high-pressure melamine plant. For example they originate from a melamine synthesis reactor, a stripper, an ageing vessel or a melt cooler or from a plurality of these apparatuses or piping. The off-gases principally consist of ammonia and carbon dioxide together with small amounts of melamine and possibly other minor components, for example urea, ureidomelamine or melam.

The off-gases are introduced into the off-gas scrubber at a temperature which is between the pressure-dependent melting point of melamine and about 500° C., preferably between about 360 and 400° C., and at a pressure of about 50 to 600 bar, preferably from about 70 to 400 bar.

The off-gas scrubber is preferably operated at approximately the same pressure as the apparatus from which the off-gases to be purified originate. Particularly preferably it is operated at approximately the same pressure as the melamine synthesis reactor.

If the off-gases originate from a plurality of apparatuses of the high-pressure melamine plant, the operating pressure of the off-gas scrubber corresponds approximately to the pressure of the apparatus which is operated at lower pressure.

The temperature in the first stage of the off-gas scrubber is higher than the temperature in the second stage. The temperature in the first stage is from about 160 to 320° C., preferably from about 180 to 280° C. The temperature in the second stage is from about 135 to 300° C., preferably from about 150 to 270° C. In addition, it is possible to introduce gaseous carbon dioxide together with the off-gases into the off-gas scrubber. This has the advantage of promoting the formation of melamine precursors in the off-gas scrubber.

The off-gases and, optionally, carbon dioxide, are preferably introduced in finely divided form into the first stage of the off-gas scrubber; this can be achieved, for example, via an off-gas channel in an off-gas distributor. The first stage preferably extends from the scrubber bottom up to about two thirds of the apparatus height.

The level of urea melt in the urea scrubber is variable. For example, it extends up to about one quarter of the apparatus height, or higher, with it also being possible to operate the apparatus virtually flooded, with the exception of a small region for off-gas separation at the apparatus top.

The off-gases can be introduced into the first stage either below the liquid level in the first stage or above the liquid level into the gas space. If the off-gases enter below the liquid level, the off-gas line is preferably heated externally in the distributor to avoid condensation of the off-gases on the distributor wall. To prevent overheating of the surrounding melamine-precursor-containing and $NH_3$-containing recirculated urea melt, a heating jacket is provided that is insulated on the outside. For this, for example a gas-flushed annular space is suitable which is connected to the melt at the point of entry of the off-gases into the melt via nozzles at the lowest point of the gas space. In the case of carbon dioxide addition to the incoming off-gases, it can be added, expediently, in the distributor and the carbon dioxide can also serve as purge gas, in addition to promoting the melamine precursor formation. If no carbon dioxide is added, the purge gas used can, for example, alternatively be ammonia or any other inert gas. The temperature of the carbon dioxide, ammonia or inert gas fed should preferably be between the off-gas temperature and the urea melt temperature of the first stage.

In the first stage of the off-gas scrubber, the off-gases introduced, optionally mixed with carbon dioxide or a purge gas, contact in countercurrent the melamine-precursor-containing and $NH_3$-containing recirculated urea melt. The contacting can also proceed in cross flow. Recirculated urea melt is taken to mean a mixture of urea melt from the second stage and urea melt recirculated via the circuit to the first stage.

The recirculation of the urea melt in the first stage of the off-gas scrubber makes possible particularly intensive gas-liquid contact. The melamine-precursor-containing and $NH_3$-containing recirculated urea melt is taken off at the bottom of the urea scrubber and divided into two portions. The first portion is fed back to the off-gas scrubber at the top end of the first stage into the gas space above the urea melt surface, preferably in finely distributed form. The second portion which is removed from the circuit is fed to the melamine synthesis reactor.

The circulated urea flow in the first stage and the transport of the melamine-precursor-containing and $NH_3$-containing recirculated urea melt to the melamine synthesis reactor can be effected, for example, by using a pump or by utilizing the difference in density between the bubble-free recirculated urea flow and the two-phase flow in the scrubber bottom, in accordance with the air-lift pump principle. The recirculation rate is preferably a multiple of the fresh urea rate. To remove energy, a heat exchanger is preferably connected into the circuit. It can be constructed either as an internal heat exchanger in the off-gas scrubber, or else as an external heat exchanger. Preferably, an external heat exchanger is used. The heat removed at the heat exchanger can, if appropriate, be used for generating steam. The temperature in the first stage of the off-gas scrubber is controlled via the energy removal at the heat exchanger, and the temperature in the second stage is co-influenced indirectly.

As a result of the intensive contact between the melamine-precursor-containing and $NH_3$-containing recirculated urea melt and the off-gases introduced, an energy transfer and mass transfer from the off-gases to the urea melt of the first stage occur. The energy transfer proceeds in the form of release of heat from the off-gases to the urea melt, which is preheated as a result. A portion of this heat is converted into chemical energy with the formation of melamine precursors, for example ammeline, ammelide or cyanuric acid. The conversion of heat energy of the off-gases into chemical energy of the melamine precursors is desirable, since in this manner the heat to be removed via the heat exchanger of the urea circuit, that is to say the heat losses in the melamine synthesis reactor/off-gas scrubber system, are decreased. The extent of melamine precursor formation is greater, the higher the temperature in the first stage of the off-gas scrubber, and in addition, also, the simultaneous introduction of gaseous carbon dioxide together with the off-gases can increase the precursor formation. The extent of melamine precursor formation in the off-gas scrubber is, due to the viscosity increase and transport problems possibly resulting therefrom of the melamine-precursor-containing and $NH_3$-containing recirculated urea melt to the melamine synthesis reactor and in the urea circuit, restricted, or, depending on plant design, variable, with increasing temperature. The residence time required for the desired melamine precursor formation in the urea melt is set by the design of the urea circuit of the first stage.

The mass transfer between the off-gases and the urea melt takes place in the form of removing a large part of the melamine and the residual minor components, for example ureidomelamine or melam, from the off-gases in the first stage of the off-gas scrubber. Because of their low crystallization temperatures, these substances are absorbed in the cooler recirculated urea melt. As a result of the relatively high temperature and the ammonia present in the recirculated urea melt of the first stage, these minor components separated from the off-gases can be converted, together with the urea, in part into melamine precursors.

Depending on the pressure and temperature conditions in the off-gas scrubber, in the urea melt of the first stage, in addition, small amounts of by-products, for example carbamate and water, can be present. They are formed by condensation of ammonia and carbon dioxide of the off-gases, the extent of by product formation being greater, the lower the temperature in the off-gas scrubber. The melamine-precursor-containing and $NH_3$-containing recirculated urea melt fed from the first scrubber stage to the melamine synthesis reactor has a temperature of from about 160 to 320° C.; in addition to the minor components separated from the off-gases it has a certain content of melamine precursors and optionally small amounts of by-products and is preferably ammonia-saturated. Owing to the ammonia content of the recirculated urea melt from the off-gas scrubber, it is not generally necessary to feed additional ammonia to the melamine synthesis reactor.

The off-gases ascending through the recirculating urea melt of the first stage enter into the second stage above the spraying apparatus of the recirculated urea melt. If appropriate, in the second stage, for example at its bottom end, an apparatus for fine separation of the minor component still present in the off-gases can be installed. It is also possible to use a plurality of separation apparatuses, for example one or more sieve trays or valve trays can be used.

In the second stage of the off-gas scrubber, the off-gases contact in countercurrent the fresh urea melt which is fed at the top of the scrubber and which can come directly from a urea plant. The contacting can also proceed in cross flow. The fresh urea melt is fed at a temperature of about 135 to 180° C., preferably in finely divided form, for example via spraying nozzles. The intensive contact between the ascending hot off-gases and the cold fresh urea causes the final separation of virtually all minor components still present in the off-gases. Furthermore, here, the cooling of the off-gases takes place to the desired end temperature of about 170 to 250° C.

The purified off-gases, principally consisting of ammonia and carbon dioxide, are taken off at the top of the off-gas scrubber and are then preferably recycled to a urea plant.

It is also possible to divide the fresh urea melt fed in the second stage into a plurality of substreams and to introduce the individual substreams at differing heights, for example, into the second stage of the off-gas scrubber.

Owing to the efficiency of the inventive off-gas purification, it is also possible to use only a part of the urea melt fed in total to the melamine synthesis reactor for the off-gas purification and to introduce the second part of the urea melt, for example, as fresh urea melt, directly from the urea plant into the melamine synthesis reactor. As a result the amount of by-products introduced into the melamine synthesis reactor can be further decreased while at the same time in the inventive off-gas scrubber the desired melamine precursors are formed.

The off-gas scrubber used can be any two-stage apparatus, as is customary, for example, for dust separation or absorption. For example, spray towers, packed columns, bubble columns, plate columns, trickling-film columns or sedimentation columns can be used for one, a plurality of, or all scrubber stages.

Preference is given to the off-gas scrubber having a heating apparatus, for example having steam jacket heating. The heat exchanger used is, for example, a tube bundle heat exchanger.

Figure 1:
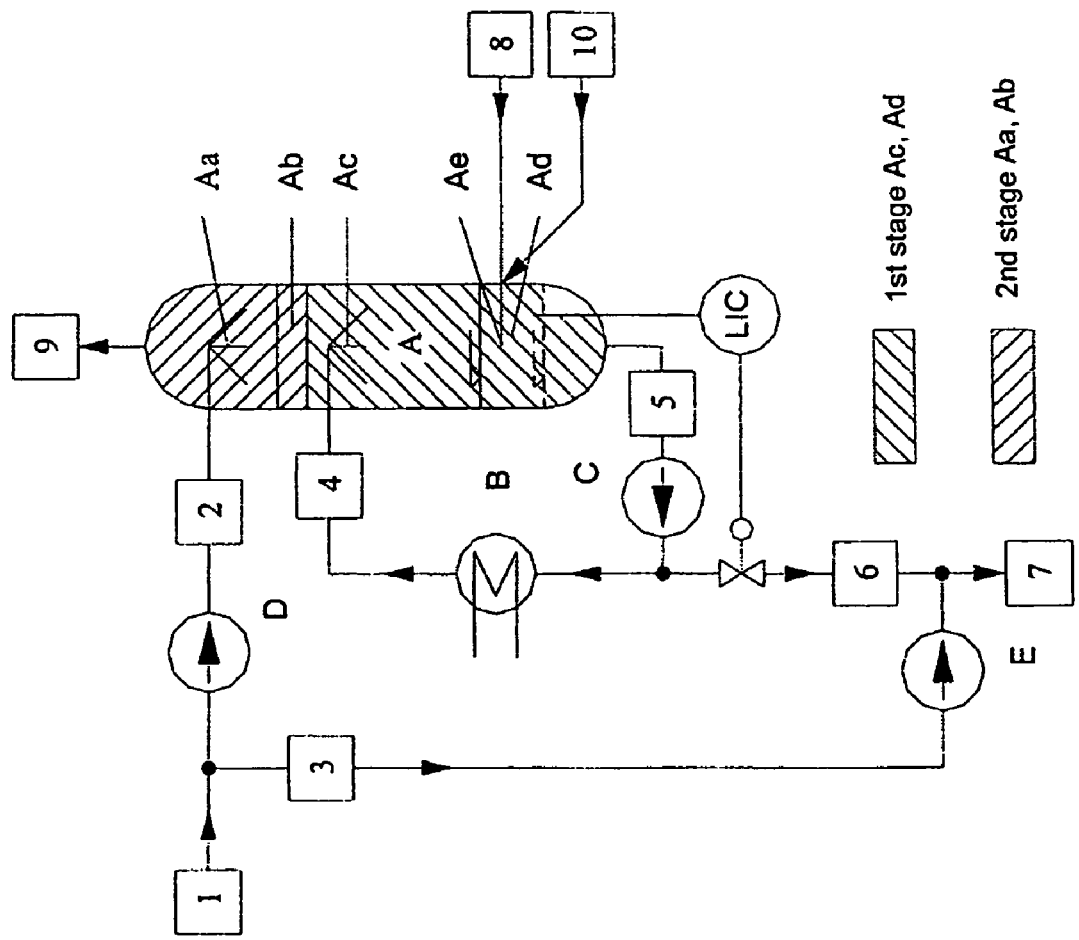
FIG. 1 is a process flow diagram for a two stage off-gas scrubber according to the present invention.

A preferred embodiment of the present invention will now be described with reference to the accompanying drawing:

FIG. 1 shows an example of a two-stage off-gas scrubber A corresponding to the present invention.

The lower first stage of the scrubber consists, in its upper section, of a lower spraying tower Ac in which the melamine-precursor-containing and $NH_3$-containing urea melt is fed from the circuit. In the lower section of the first stage is situated the off-gas distributor Ae which opens out into the off-gas scrubber either above or below the level of the melamine-precursor-containing and $NH_3$-containing recirculated urea melt. If the off-gas distributor is situated below the level, there is an additional bubble column section Ad at the apparatus bottom of the first stage.

The upper second stage of the off-gas scrubber is subdivided into an upper spraying tower Aa and one or more sieve trays Ab for intensive scrubbing of the off-gases ascending from the first stage. In the second stage the off-gases are purified with fresh urea melt at relatively low temperature.

The fresh urea feed stream 1 divides into the scrubber fresh urea feed stream 2 which flows into the off-gas scrubber at the top via a distributor and the bypass fresh urea stream 3 which leads directly into the melamine synthesis reactor. In this case the fresh urea stream 3 which has bypassed the off-gas scrubber can either be added to the urea melt stream removed from the circuit 6 from the off-gas scrubber upstream of entry into the melamine synthesis reactor and passed into the melamine synthesis reactor as melamine synthesis feed stream 7, or passed into the melamine synthesis reactor as a separate urea melt stream.

The fresh urea feed stream 1 is quantitatively divided via the controllable fresh urea feed pump D and the controllable bypass fresh urea pump E. By means of the recirculated urea pump C, a melamine-precursor-containing and $NH_3$-containing recirculated urea stream 5 is taken off at the bottom of the first stage of the off-gas scrubber, which recirculated urea stream 5 is divided into the scrubber recirculated urea stream 4 and the urea melt stream removed from the circuit 6. The scrubber recirculated urea stream 4 is recirculated to the first stage via the heat exchanger B by means of a distributor. The urea melt stream removed from the circuit 6 which controls the level in the off-gas scrubber via the level controller LIC is fed, after mixing with the bypass fresh urea stream 3, as melamine synthesis feed stream 7 to the melamine synthesis reactor.

The purified off-gases leave the off-gas scrubber at the top via the off-gas outlet 9 in the direction of the urea plant.

The hot off-gases coming from the high-pressure melamine plant are introduced into the scrubber at the off-gas inlet 8 in the lower part of the off-gas scrubber via the off-gas distributor Ae below the distributor for the scrubber-recirculated urea stream 4. Simultaneously with the off-gases, carbon dioxide is fed to the off-gas scrubber via the carbon dioxide feed 10.

FIG. 2 shows a section through the off-gas distributor Ae.

It consists of an externally heated off-gas central tube having downwards directed gas outlet channels. The heating jacket of the off-gas central tube is separated from the surrounding urea melt by means of a heat-insulating, gas-flushed annular space. The annular space is connected to the gas exit of the off-gas channel via nozzle bore holes at the lowest point.

In this manner the heat released from the heating medium to the urea melt is kept as low as possible to prevent substantially the pyrolysis of the urea which proceeds at relatively high temperatures and would lead to the formation of pyrolysis products.

The table below shows the comparison between the single-stage process and the inventive two-stage process for off-gas purification.

|  | Single-stage process | | Two-stage process | |
| --- | --- | --- | --- | --- |
| Temperature | Off-gas | Urea | Off-gas | Urea |
| Inlet | 370° C. | 150° C. | 370° C. | 150° C. |
| Transition first/second stage | — | — | 242° C. | 205° C. |
| Exit | 205° C. | 205° C. | 205° C. | 242° C. |
| Specific waste heat | 33 kJ/mol urea | | 24 kJ/mol urea | |
| Content of melamine precursors and condensed melamine in the urea melt fed to the melamine synthesis reactor | 4% | | 7% | |

For the same off-gas inlet temperature, fresh urea inlet temperature, off-gas exit temperature and for the same pressure in the two scrubber variants, for the two-stage off-gas scrubber having differing operating temperatures in the two stages, for the same efficiency of off-gas purification, there results improved urea preheating, reduced specific waste heat losses and increased melamine precursor formation, which corresponds overall to an improved energy efficiency of the overall process.

Figure 3:
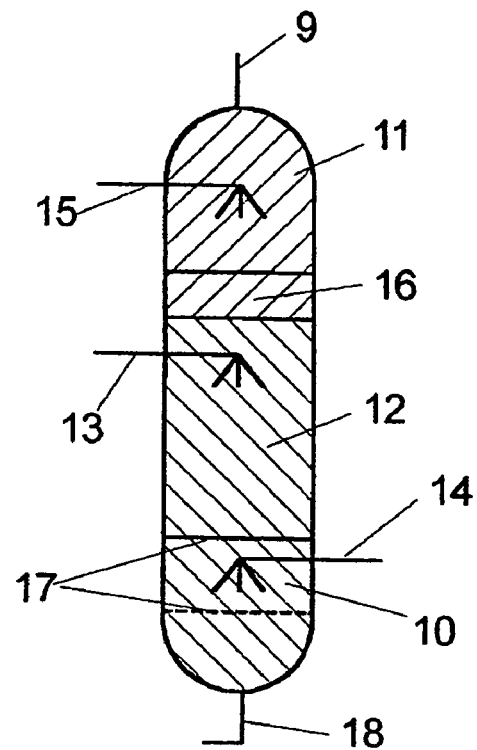
FIG. 3 is a process flow diagram of an off-gas scrubber.

FIG. 3 shows a diagrammatic section of a gas scrubber as used for purifying contaminated gases. Advantageously, the gas scrubber is utilized as off-gas scrubber for carrying out the inventive process.

The gas scrubber consists of two stages which are disposed one above the other. In the upper section of the lower stage (12) there is situated a spraying tower (13), through which a melt is fed. In the lower part of the lower stage there is situated the gas distributor through which the gas to be purified is introduced. In the inventive process, the off-gases to be purified are introduced through the gas distributor.

In the upper part of the upper stage (11) there is disposed a further spraying tower (15) through which the melt, in the invention urea melt, is fed. Opposite the spraying tower (15) are situated one or more sieve trays for intensive scrubbing of the gases ascending from the lower stage. The purified gases are taken off at the top of the gas scrubber and the melt is taken off at the bottom of the lower stage.

In a preferred embodiment of the gas scrubber it is possible, in addition to the gas distributor in the lower section of the lower stage, to provide one or more further gas feeds.

It is also within the context of the invention to equip the gas scrubbers with heating jackets.

Figure 4:
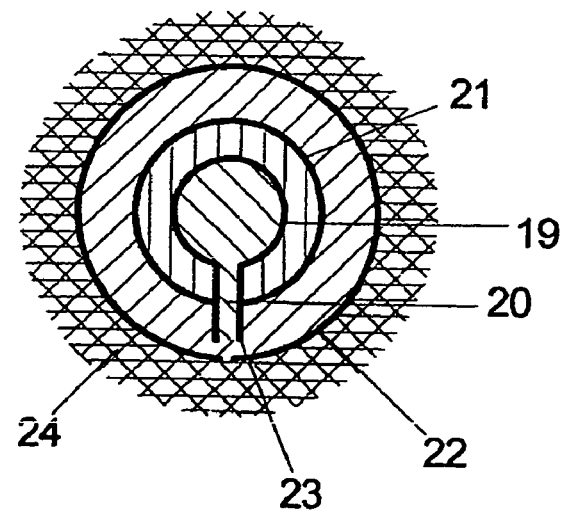
FIG. 4 is a schematic diagram of an off-gas distributor shown in section.

FIG. 4 shows a section through the gas distributor.

The gas distributor consists of a central gas tube (19) which is surrounded by a heating jacket (21). This design substantially avoids heat loss of the gases to be purified. The heating jacket (21) is surrounded by a thermal insulating medium, preferably by a gas-purged annular space for insulating the heating jacket (21) from the melt. The gas can exit from the gas distributor into the melt via nozzle bore holes.

The nozzle bore holes can be formed as gas exit channel via two parallel metal sheet strips which are welded onto the central gas tube (19) perpendicularly to the two slot edges.

The invention claimed is:

1. A process for purifying off-gases from a high-pressure melamine plant with formation of melamine precursors, characterized in that
   the off-gases are brought into contact in a first stage with melamine-precursor-containing and $NH_3$-containing recirculated urea melt and
   in a second stage with fresh urea melt.

2. The process according to claim 1, characterized in that the melamine-precursor-containing and $NH_3$-containing recirculated urea melt is a mixture of urea melt from the second stage and urea melt recirculated via the circuit to the first stage.

3. The process according to claim 1 or 2, characterized in that a portion of the melamine-containing and $NH_3$-containing recirculated urea melt is fed to the melamine synthesis reactor.

4. The process according to claim 1, characterized in that the off-gases are purified at a pressure of from 50 to 600 bar.

5. The process according to claim 1, characterized in that the off-gases are purified in the first stage at a temperature of from 160 to 320° C.

6. The process according to claim 1, characterized in that the off-gases are purified in the second stage at a temperature of from 135 to 300° C.

7. The process according to claim 1, characterized in that the first stage comprises an internal or external heat exchanger for energy removal.

8. The process according to claim 1, characterized in that carbon dioxide is added to the off-gases.

9. The process according to claim 1, characterized in that the off-gases are introduced via an off-gas distributor above or below the liquid surface of the melamine-precursor-containing and $NH_3$-containing recirculated urea melt of the first stage.

10. The process according to claim 1, characterized in that the fresh urea melt is divided in the second stage into a plurality of substreams and introduced at different heights.

11. The process for preparing melamine, characterized in that a mixture of fresh urea melt and melamine-precursor-containing and $NH_3$-containing recirculated urea melt is fed to the melamine synthesis reactor.

12. The gas scrubber, in particular an off-gas scrubber for purifying contaminated gases, in particular for carrying out the process according to claim 1 having upper and lower stages (11, 12) disposed one above the other, wherein an upper section of the lower stage includes a spraying tower (13) and a lower section of the lower stage includes a gas distributor (14) and an upper section of the upper stage (11) comprises a spraying tower (15) and one or more sieve trays (16) disposed opposite the spraying tower, the purified gases being taken off at the top of the gas scrubber and the melt being take off at the bottom of the lower stage.

13. The gas scrubber according to claim 12 having a further gas feed in the lower part of the lower stage.

14. The gas scrubber according to claim 12 or 13 having a heating jacket.

15. A gas distributor for feeding gases into a melt having a central tube (19) which is surrounded by a heating jacket (21) which is separated from the melt by a thermal insulating medium, in particular by a gas-purged annular space, having nozzle bore holes for the gas exit.

* * * * *